(12) United States Patent
Trumbull

(10) Patent No.: US 6,228,051 B1
(45) Date of Patent: *May 8, 2001

(54) LAPAROSCOPIC SEALANT APPLICATOR

(75) Inventor: Horace R. Trumbull, Skillman, NJ (US)

(73) Assignee: Bristol-Myers Squibb Company, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/049,859

(22) Filed: Mar. 27, 1998

Related U.S. Application Data

(60) Provisional application No. 60/042,549, filed on Mar. 27, 1997.

(51) Int. Cl.[7] ................................................. A61M 37/00
(52) U.S. Cl. ................................ 604/95; 604/23; 604/528
(58) Field of Search ..................................... 606/213–215, 606/108; 604/95, 264, 528, 19, 23, 26, 48; 600/136–142, 146–151, 156

(56) References Cited

U.S. PATENT DOCUMENTS

| | | | |
|---|---|---|---|
| 5,318,524 | 6/1994 | Morse et al. | 604/82 |
| 5,383,899 | 1/1995 | Hammerslag | 606/214 |
| 5,728,132 | 3/1998 | Van Tassel et al. | 606/213 |
| 5,741,223 | 4/1998 | Janzen et al. | 604/15 |
| 5,746,755 | 5/1998 | Wood et al. | 606/148 |

FOREIGN PATENT DOCUMENTS 9807372  2/1998  (WO).

*Primary Examiner*—Mark Bockelman
*Assistant Examiner*—Deborah Blyveis
(74) *Attorney, Agent, or Firm*—Theodore R. Furman, Jr.; John M. Kilcoyne; Stuart E. Krieger

(57) ABSTRACT

A laparoscopic applicator device for the selective directional application of one or more liquids to a surgical site is disclosed. The device comprises a handle with liquid inlets at one end, discrete channels within one or more tubes connecting with said inlet and exteding through said handle to a nozzle, and a dual injection shaft at the nozzle end for inserting the shaft and nozzle through a surgical trocar. The dual shaft comprises s rigid portion immediately adjacent the handle and a flexible portion near the nozzle tip. Means are provided, preferably within the handle, for the controlled articulation of the flexible shaft/nozzle assembly, thereby providing application of the liquids in a desired direction. The present invention is particularly useful in the application of surgical sealants, e.g., fibrin sealants. Methods of applying such components are also a part of the invention.

7 Claims, 3 Drawing Sheets

LAPAROSCOPIC SEALANT APPLICATOR

This application claims benefit to U.S. provisional application Ser. No. 60/042,549, filed Mar. 27, 1997.

FIELD OF THE INVENTION

This invention relates to a laparoscopic sealant applicator wherein a multi-lumen tubing, in fluid communication with a source of sealant, extends a suitable distance beyond a handle so that the tubing can be laparoscopically inserted and articulated in a desired direction to a desired site.

PCT/US96/19505, entitled A Method of Applying a Mixture of Two Liquid Components as well as a Device for Carrying Out the Method, filed Dec. 6, 1996, discloses an applicator device for applying a surgical sealant, e.g., a fibrin sealant, to a desired site. The applicator consists of a relatively thin multi-lumen tubing which is in fluid communication with sources of sealant components at one end and forms, or is connected to, a spray tip at the other end. In a preferred embodiment, the tubing runs through a handle at or near the spray tip end. The handle is the part of the instrument held by the surgeon to apply the sealant and it may include activating means for actuating the spray from the component sources.

Sealants would also be useful in laparoscopic procedures.

SUMMARY OF THE INVENTION

In accordance with the present invention a laparoscopic applicator device for the selective directional application of one or more liquids to a surgical site is disclosed. The device comprises a handle with liquid inlets at one end, discrete channels within one or more tubes connecting with said inlets and extending through said handle to a nozzle, and a dual insertion shaft at the nozzle end for inserting the shaft and nozzle through a surgical trocar. The dual shaft comprises s rigid portion immediately adjacent the handle and a flexible portion near the nozzle tip. Means are provided, preferably within the handle, for the controlled articulation of the flexible shaft/nozzle assembly, thereby providing application of the liquids in a desired direction. The present invention is particularly useful in the application of surgical sealants, e.g., fibrin sealants. Methods of applying such components are also a part of the invention.

DETAILED DESCRIPTION OF THE PREFERRED EMBODIMENTS

The present invention provides a useful device for the laparoscopic application of one or more liquid components to a surgical site. Preferably, the components form a surgical sealant, e.g., a fibrin sealant and the present invention will be further disclosed with regard to fibrin sealants. The device is designed to be utilized through a surgical trocar and facilitates the selective directional application of fibrin sealants via the controlled articulation of a flexible portion of an insertion shaft, including a dispensing tip or spray nozzle.

Figure 1:
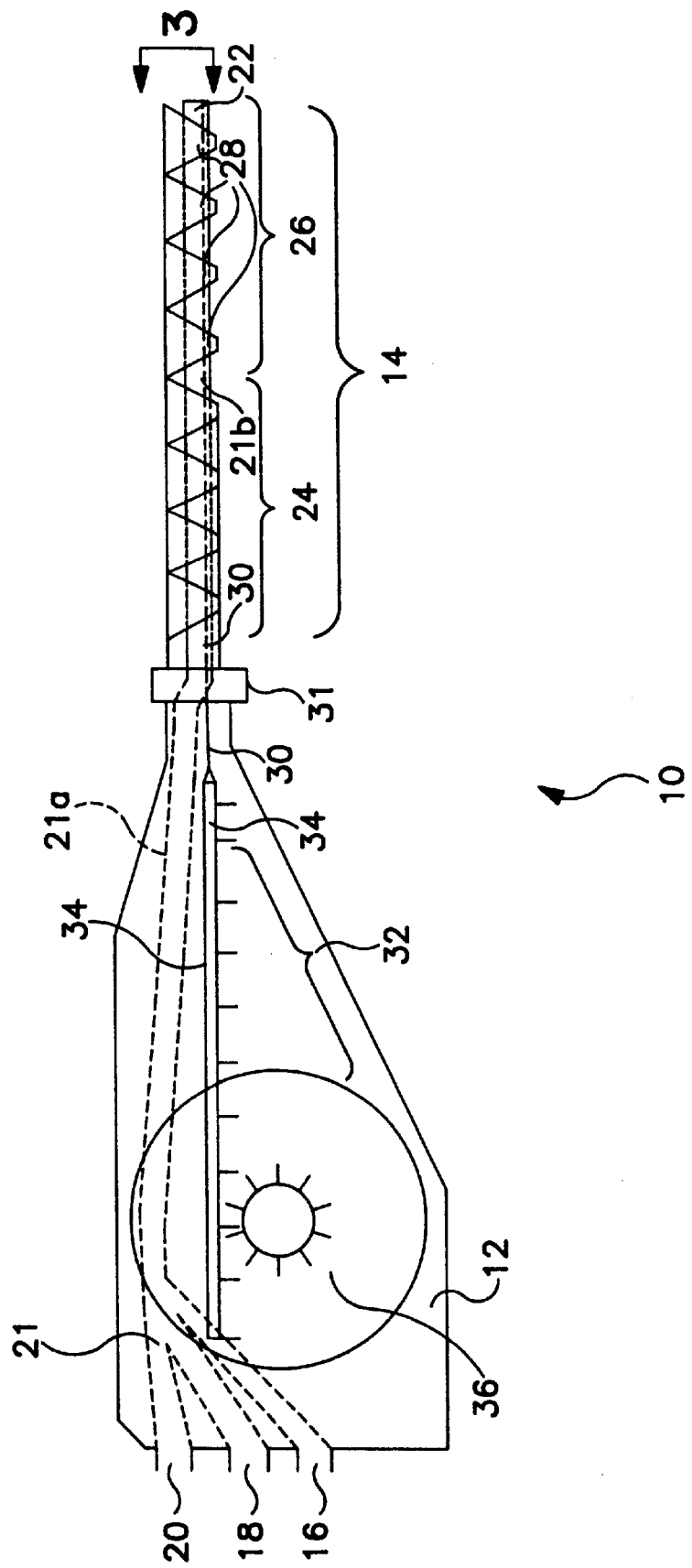
FIG. 1 shows a lateral partial cross sectional view of the laparoscopic applicator device of the present invention.
Figure 2A:
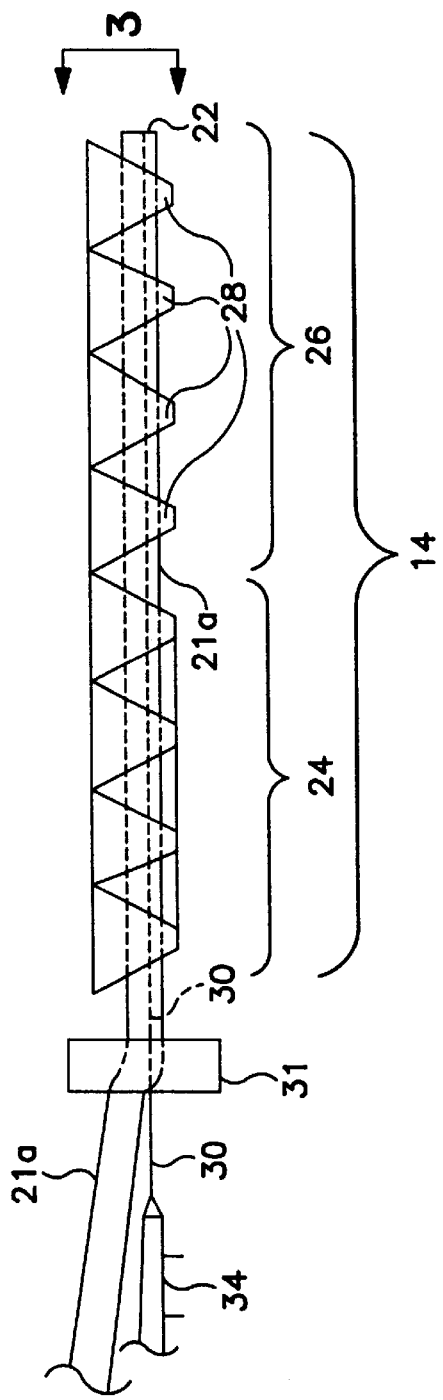
FIGS. 2a and 2b illustrate the inarticulated and fully articulated arrangement of wedges incorporated into the shaft.
Figure 2B:
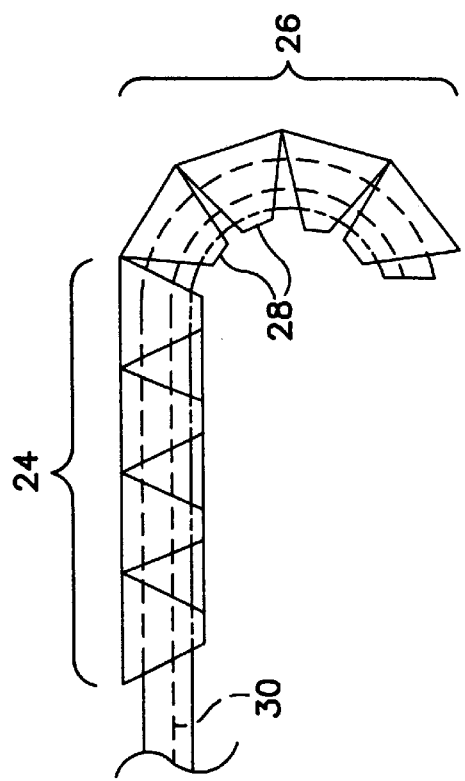

FIG. 1 shows a device 10 of the present invention which includes a handle 12 and an insertion shaft 14 adapted to be insertable through a surgical trocar. At a first end of the handle 12 are inlets 16, 18, 20 for the one or more liquid or sealant components and optional gas component where spray application is desired. Any number of inlets may be provided. The inlets 16, 18, 20 are adapted to receive the liquid/gas components, and sources (not shown) of the components may be directly adjacent to inlets or may be remote from said inlets but in fluid communication with the inlets via supply tubing. A tubing means 21 extends from the inlets through the handle 12 and insertion shaft 14 to a nozzle or applicator tip 22. This provides for the liquid/gas components to be delivered from the sources to, and out of, the nozzle 22 preferably activated by a separate means controlling the actual flow of liquid and gas. Preferably, the insertion shaft 14 is enclosed with a cladding (not shown) suitable for endoscopic and laparoscopic use. FIG. 1 further illustrates that the invention shaft 14 is a two-part assembly comprising a rigid shaft 24 integral with a second end of the handle 12 and a flexible shaft 26 integral with the rigid shaft 24 and preferably coextending and continuous with the tubing means 21 and nozzle 22. The flexible shaft 26 includes a series of hinges 28 which are interconnected so as to enable the bending of the flexible shaft 26 in one direction and straightening of the flexible shaft 26 to its original position. Preferably, the hinges 28 are wedges pivotally interlocked at their tops and disposed laterally along one or both sides of the portion of the tubing means which is included within the flexible shaft 26. The present device further comprises a means for articulating the hinges 28 and flexible shaft through its bent and straightened positions which preferably includes a control or push/pull wire 30 connected at a first end at or in the nozzle 22 of the tubing means 21 and running through or along the tubing means to a control means 32 within said handle 12 for controlling the articulation of the nozzle 22. If the wire 30 runs through the tubing means 21, then the wire 30 and tubing means intersect at a manifold 31. This provides a juncture at which the wire 30 exits the tubing means 21 to engage the control means 32. Thus, the tubing means would comprise a wireless portion 21a and a wire containing portion 21b in fluid communication with each other via manifold 31. Optionally, the control means can be a remote manually operated or foot pedal-operated system. The control means 32 preferably comprises a rack and pinion assembly comprising a rack 34 (or tooth-containing element) engaged with a rotable pinion or knob 36, such that rotation of the knob 36 extends or retracts the wire 30 which in turn articulates or straightens the flexible shaft 26. This articulation is illustrated in FIG. 2a and 2b. FIG. 2a illustrates the relative position of the hinges or wedges 28 when the wire 30 is retracted or withdrawn by the control knob (not shown). FIG. 2b illustrates the relative position of the hinges or wedges 28 when the wire (not shown) is extended by the control knob and the wedges and tubing (not shown) are allowed to fold down upon themselves. The degree of extension/retraction dictates the degree of articulation.

Figure 3:
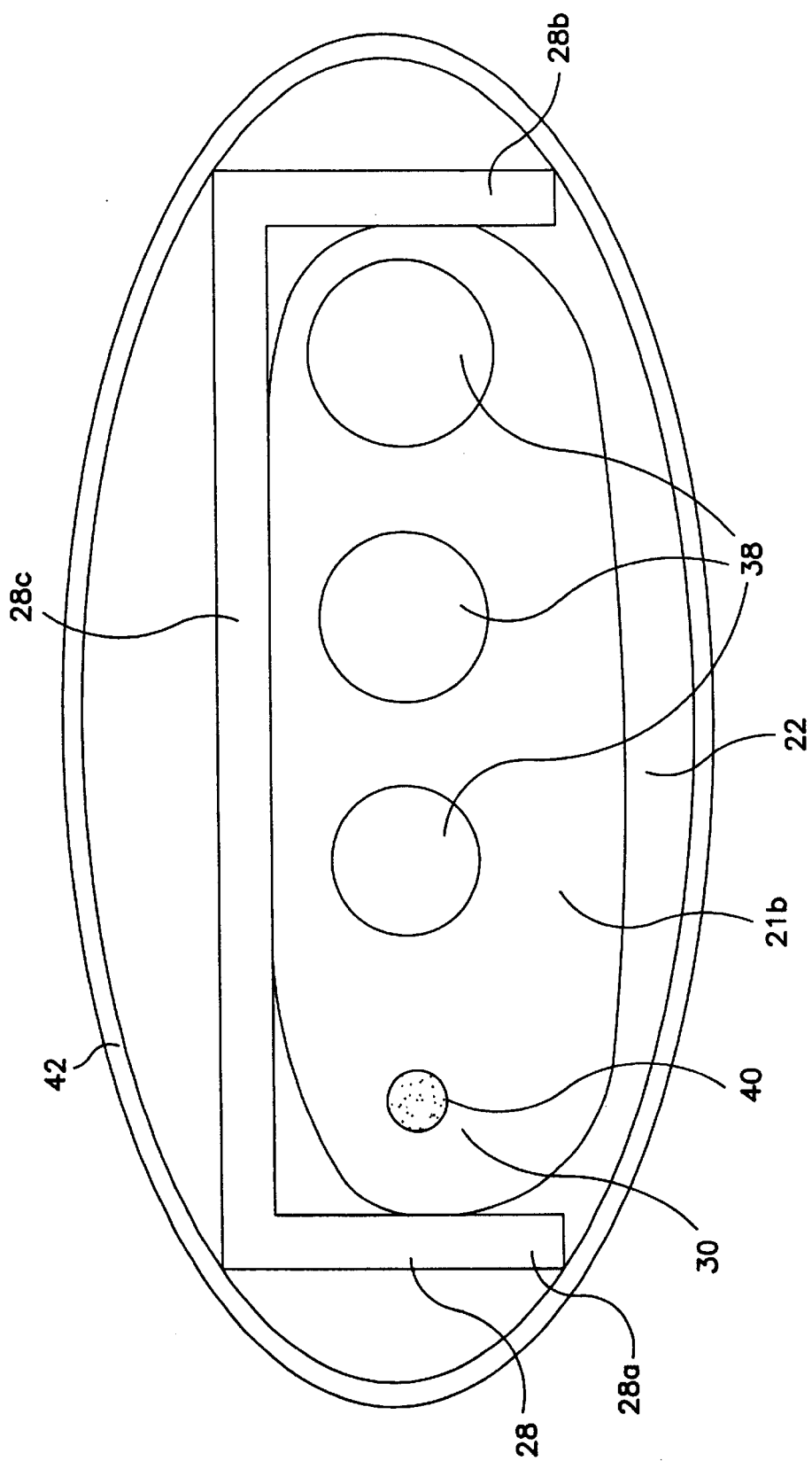
FIG. 3 is an end view of the nozzle of the present invention.

FIG. 3 shows an end view of the nozzle 22 of the device of the present invention. The nozzle 22 includes outlets 38 corresponding by fluid communication via discrete channels in the tubing means to inlets 16, 18 and 20. The outlets 38 for liquids and optionally a gas for spray are shown arranged within the end wedge 28 which preferably comprises wedges 28a and 28b on either side of the so-arranged outlets 38 and further includes a bridging portion 28c. Preferably, the outlets 38 and attached end 40 of the wire 30 are incorporated within the preferred single tubing means 21b, although individual tubes can be employed. As can be seen the preferred tubing means 21 comprises the tubing means and having integral channels therein which terminate in the outlets 38 on the nozzle 22. The tube can be of any flexible material, e.g., plastic material, suitable for such medical purposes. The nozzle 22 can be a separate component or can just be the open end of the tube 21b. A cladding 42 can be placed around the entire nozzle/tubing assembly as shown and preferably extends the length of the insertion shaft 14, i.e., the rigid shaft 24 and the flexible shaft 26. The cladding can be of any convenient material utilized in endoscopic and laparoscopic devices.

Preferably, this is a single patient use, disposable device. It is intended that the flexible shaft and the rigid shaft (typically, a total of about 12 cm in length) are the parts of the device which are to be passed into and through the trocar. It is intended that the maximum cross sectional measurement of any part of the rigid or flexible shaft shall be chosen, so that the device can be used with commercially available trocars.

Although any liquid components can be used, the present invention is particularly well-suited for surgical sealant, e.g., fibrin sealant application. A preferred sealant is disclosed by Edwardson et al. In EP 592242 which employs a low pH4 fibrin monomer composition co-applied with a ph10 acetate buffer.

What is claimed is:

1. An applicator device for the directional laparoscopic deliver of a surgical sealant to a surgical site comprising:

a plurality of separate liquid components of a surgical sealant;

a tubing member including a conveyance channel for each of said liquid components, said tubing member having an outlet portion, said outlet portion including a nozzle for dispensing said liquid components, each of said conveyance channels being adapted to convey a liquid component to said nozzle;

a handle having said outlet portion of said tubing member extending therefrom;

a two-part insertion shaft surrounding at least part of said outlet portion of said tubing member, said two-part insertion shaft including a rigid shaft part secured to said handle, and a flexible articulatable shaft part extending from said rigid shaft part and surrounding at least part of said outlet portion of said tubing member, and directionally controllable, a articulating means extending from said handle through said tubing member for controlling directional articulation of said nozzle dispensing said liquid components to a surgical site.

2. The applicator device of claim 1 wherein said flexible shaft part has a length and said directionally controllable, articulating means comprises:

(a) a series of interconnected hinges laterally disposed along the length of said flexible shaft part;

(b) a push/pull wire connected to and extending from said nozzle, through said tubing member and into the handle; and (c) a control member within said handle connected to a second part of said push/pull wire such that actuation of said control member provides for the desired degree of articulation in said flexible shaft part to apply said liquid components in a desired direction.

3. The applicator of claim 2 wherein said hinges comprise wedges of a rigid material disposed along said flexible shaft part.

4. The applicator of claim 2 wherein said control member comprises a rack and pinion assembly integral with said second end of said push/pull wire and a control knob or activator.

5. The applicator of claim 1 wherein each of said liquid components has its own source.

6. The laparoscopic applicator of claim 1 wherein said surgical sealant is a fibrin sealant.

7. The applicator of claim 1 further incorporating a gas to spray said sealant.

* * * * *